United States Patent
Wahlig et al.

(10) Patent No.: US 6,796,701 B2
(45) Date of Patent: Sep. 28, 2004

(54) PREPARATION AND APPLICATION DEVICE FOR IMPLANT MATERIALS WITH HAND-OPERATED PUMP

(75) Inventors: Helmut Wahlig, Darmstadt (DE); Elvira Dingeldein, Dreieich (DE); Edgar Wüst, Rodgau (DE); Christoph Sattig, Dieburg (DE)

(73) Assignee: Coripharm Medizinprodukte GmbH & Co. KG, Dieburg (DE)

( * ) Notice: Subject to any disclaimer, the term of this patent is extended or adjusted under 35 U.S.C. 154(b) by 116 days.

(21) Appl. No.: 10/204,390

(22) PCT Filed: Feb. 23, 2001

(86) PCT No.: PCT/EP01/02042

§ 371 (c)(1),
(2), (4) Date: Aug. 20, 2002

(87) PCT Pub. No.: WO01/70146

PCT Pub. Date: Sep. 27, 2001

(65) Prior Publication Data

US 2003/0021180 A1 Jan. 30, 2003

(30) Foreign Application Priority Data

Feb. 28, 2000 (DE) .................................. 200 03 676 U
Mar. 22, 2000 (DE) .................................. 200 05 333 U

(51) Int. Cl.⁷ .............................................. B01F 13/06
(52) U.S. Cl. ..................................................... 366/139
(58) Field of Search ................................ 366/139, 189, 366/244–247, 255–256, 332–333; 206/219–222

(56) References Cited

U.S. PATENT DOCUMENTS

| | | | |
|---|---|---|---|
| 4,277,184 A | | 7/1981 | Solomon |
| 5,328,262 A | | 7/1994 | Lidgren et al. |
| 5,435,645 A | * | 7/1995 | Faccioli et al. ............. 366/130 |
| 5,443,182 A | * | 8/1995 | Tanaka et al. .............. 366/139 |
| 5,549,380 A | | 8/1996 | Lidgren et al. |
| 5,551,778 A | | 9/1996 | Hauke et al. |
| 5,588,745 A | * | 12/1996 | Tanaka et al. .............. 366/130 |
| 5,788,463 A | * | 8/1998 | Chan |
| 5,934,803 A | * | 8/1999 | Hutter .......................... 366/139 |
| 6,536,937 B1 | * | 3/2003 | Burchett ..................... 366/139 |

FOREIGN PATENT DOCUMENTS

| | | | |
|---|---|---|---|
| DE | 350330 | | 3/1922 |
| DE | 2801706 | * | 7/1979 |
| DE | 83 27 292.5 | | 1/1984 |
| DE | 3640279 | * | 6/1987 |
| DE | 40 30 832 | | 7/1991 |
| DE | 4302230 | * | 8/1993 |
| DE | 4228780 | * | 3/1994 |
| EP | 674888 | * | 10/1995 |
| EP | 692229 | * | 1/1996 |
| EP | 768067 | * | 4/1997 |
| EP | 796653 | * | 9/1997 |
| EP | 882436 | * | 12/1998 |
| EP | 402669 | * | 12/1999 |
| WO | 90/13264 | * | 11/1990 |
| WO | 94/26403 | * | 11/1994 |
| WO | 97/18031 | * | 5/1997 |
| WO | 99/67015 | * | 12/1999 |

* cited by examiner

Primary Examiner—Charles E. Cooley
(74) Attorney, Agent, or Firm—Norris McLaughlin & Marcus P.A.

(57) ABSTRACT

A preparation and application device for implant materials consisting of at least one powder or granulate component and one liquid component, which are to be prepared immediately before use, is disclosed. The device comprises a first container which holds the powder or granulate component in a sterile, closed-off manner; and a second container which holds the liquid component in a sterile, closed-off manner and which can be connected to the first container. A mixing shaft which is hollow and located on a mixing mechanism is guided out of the first container is hollow and joins a hand pump for producing negative pressure at its external end. A measuring device which indicates the negative pressure can be connected to the first container and the housing of the hand pump is configured in such a way that it is suitable for use as a handle for moving the mixing shaft.

9 Claims, 1 Drawing Sheet

PREPARATION AND APPLICATION DEVICE FOR IMPLANT MATERIALS WITH HAND-OPERATED PUMP

BACKGROUND OF THE INVENTION

The invention relates to a preparation and application device for implant materials to be prepared from at least one powder or granulate component and one liquid component immediately before use. The device includes a first container which holds the powder or granulate component in a sterile, sealed manner; and a second container which holds the liquid component in a sterile, sealed manner and can be connected to the first container. Means are provided for producing an overflow connection between the two containers, for forcing the liquid component out of the second container and into the first container and for intimately, homogeneously mixing the components in the first container by moving a mixing device which is located in the first container on a mixing shaft that is guided out of the container in a sealed manner. The first container is configured in such a way that it can be connected to a source of negative pressure.

During the last years, minimal-invasive treatment methods have become more and more important for the surgical treatment of defects on the skeletal system. Certain methods are used in particular in orthopedics and accident surgery, wherein the treatment is performed partially under x-ray control and involves, for example, only a stab or percutaneous incision. These methods have obvious advantages over conservative open surgery: the surgery is significantly less stressful for the patient, the hospital stay is much shorter, which reduces the treatment cost. In addition, there is a significantly reduced risk of infections, which could otherwise lead to long-term and expensive complications.

In particular, during minimal-invasive treatment in the reconstruction of bone defects, filler components, stabilizing components, auxiliary and/or active components are brought percutaneously and directly to the site of the defect, where they are used particularly for filling the defects and for partial stabilization, as well as for triggering repair processes, for inducing and accelerating neovascularization and new bone formation, as well for preventing and/or treating infections in the defect area. Most of the employed materials or active ingredients, and/or their combinations, cannot be applied using conventional injection needles due to their special composition and associated consistence. It is therefore necessary to use special applicators that are adapted for a particular product, for delivering the therapeutics, i.e., the implant materials, easily and safely to the location where they are to be applied.

Of course, the implant materials, which mostly consists of several separate components, must be combined and mixed into a homogeneous matrix before they are applied.

It has been observed, however, that the chemical-physical properties of the implants, in particular their mechanical stability, are significantly affected by the particulars of the mixing process. These properties are important prerequisites for attaining optimum functionality.

This will be illustrated with reference to an exemplary implant material—bone cement—where these effects have been studied in detail:

It has been known since many years that the mechanical stability of bone cements is reduced by both larger and smaller air inclusions, which enter the cement matrix mainly at the time the cement components are mixed together. The resulting weakening of the cement can be easily measured and detected physically, considering that the cement matrix can contain up to 25% air, in particular when the components are improperly mixed by hand. The air bubbles enclosed in the cement produce pores which can cause the formation of fissures and gaps when the prosthesis is later stressed. This in turn can cause the cement jacket surrounding the prosthesis to shatter prematurely, causing the prosthesis to loosen, which can require removal of the prosthesis. Conversely, experimental and clinical studies have shown that cements that are almost air-free and therefore also nonporous tend to have a greater fatigue resistance and can therefore increase the useful life of endo-prostheses.

In addition to the above example from the technical field of bone cements, technical methods for production of ceramics will also be described. Nonporous (i.e., in particular air-free) matrices can be produced by conventional techniques, in particular when processing expensive plaster and molding materials, that attain the mechanical stability required of the end product.

Accordingly, the same conditions have to be met also for medical implant materials, for example for materials based on calcium phosphate, calcium sulfate or specific polymers, which are to provide both a physiological effect and a stabilizing function. Air inclusions have to be safely eliminated when these products are prepared and mixed, so as to ensure the desired mechanical stability of the end product of the implant material.

While such methods are commonly used in other technical fields, corresponding mixing and/or applications systems, for example for ceramic implant materials, do not yet exist in the medical field. Over the past years, these problems related to bone cements have been recognized which has led to intensive investigations of mixing systems, with the goal to develop methods that can to a large extent eliminate air inclusions in the cement when the cement components are mixed, and to develop mixing methods that guarantee reproducible and standardized mixing results.

This development will now be illustrated with reference to exemplary well-characterized bone cements: intensive investigations have led to the so-called "vacuum mixing technique," which is today generally accepted and represents the state of the art. The cement components (polymer powder and monomer liquid) are hereby mixed in specially constructed mixing vessels and/or application cartridges under reduced atmospheric pressure.

To achieve a "vacuum" (a reduced or negative air pressure) which minimizes the air content in the thoroughly mixed cement matrix, a residual pressure of approximately 100 to 200 mbar has to be maintained during the mixing process.

In practice, the cement mixing vessel is hereby sealed after the cement components have been filled in, and is connected via a hose to a pump that is powered by compressed air. Depending on the source of the compressed air and the construction of the pump, the air volume contained in the mixing system is—more or less rapidly—reduced, resulting in a correspondingly smaller residual pressure. However, not every system on the market is capable of reducing the air pressure to a point where the intended goal—namely a cement that is nearly free a pores—is also achieved in practice.

A significant problem associated with this type of "vacuum mixing" of bone cements is related not only to the sometimes quite different pump efficiencies of the pumps, but also to the often quite large variations in the hospitalinternal compressed air supply in the operating room, that is required for operating the pumps. The building pressure of the compressed air in different hospitals tends to vary not only over the course of the day, but the outlet pressure can generally range between approximately 5 and approximately 10 bar, which tends to significantly affect the pumping efficiency and therefore also the "vacuum" in the mixing vessels, and consequently also the quality of the cement as measured by the air inclusions. Standardizable and reproducible mixing results can hence not be realized in this manner.

Moreover, only a small number of the pumps operating today have a manometer that shows and controls the pumping efficiency during the mixing process. However, such measurement devices on the pumps themselves do not necessarily reflect the pressure in the actual mixing vessels. Adequate and reliable mixing results can only be obtained if the residual pressure in the mixing vessel is reliably controlled during the entire duration of the mixing process. None of the conventional "vacuum"-mixing systems includes suitable display or measurement devices on the mixing vessels themselves. Accordingly, there is no guarantee that the atmospheric pressure in the mixing container is actually lowered before and/or during the actual mixing process to the residual pressure which is necessary for obtaining the desired mixing result—namely a cement that is essentially nonporous.

This results in significant disadvantages for the processes used today and significant uncertainly in the quality of the cement and accordingly also for the long-term clinical success of the artificial joint replacement.

In addition, hospitals are increasingly making the transition to electrically powered surgical tools, so that a suitable compressed air outlet will no longer be available in the operating room.

SUMMARY OF THE INVENTION

It is therefore an object of the invention to eliminate these sources for error and incertitude, as described above with reference to exemplary "vacuum mixing" of bone cements, and more particularly, to make it practically feasible to produce nonporous matrices for other implant materials, in addition to bone cements, that are used with increasing frequency in reconstructive surgery, by providing a versatile and simple mixing and application system that is easy to handle and can be used for optimizing the preparation and the chemical-physical properties of implant materials that are to be placed in the human and/or animal body. Important applications for such a system are, in particular, in the field of orthopedics and accident surgery.

Two important aspects had to be considered before the technical goal could be met:
1. The system of the invention should guarantee the production of essentially nonporous implant materials and should be suitable not only for polymers, but in particular also for a broad range of ceramic materials.
2. The system of the invention should make it possible to easily and reliably combine the components required for producing the implant material. The entire process of combining and mixing the components should take place under sterile and airtight conditions, so that the components do not come into contact with the ambient air.

The problems of producing nonporous matrices (i.e., matrices free of air inclusions) will now be illustrated with reference to exemplary bone cements. These problems are quite general and relate to the mixing and application of different implant materials. These problems have been thoroughly investigated and documented during the past years, as far as they relate to bone cements, so that reference is made to this area. As discussed above, experimental and clinical studies have shown that conventional mixing methods for cement components, for example by using simple cup-shaped vessels and a spatula, are not only cumbersome and make it difficult to maintain an aseptic environment, but also tend to introduce large quantities of air into the cement paste in the form of larger- and smaller-size bubbles. These inclusions significantly reduce the mechanical stability of the hardened cement, in particular its "fatigue-resistance," which can cause the prosthesis to malfunction prematurely.

The so-called open mixing—as described above—has additional practical disadvantages. Because the cements are mostly packaged in a separate bag for the powder and a separate glass container for the liquid, the powder or liquid can easily be spilled when the components are poured into the mixing vessel. Accordingly, the quantity of powder and liquid may then no longer be exactly matched which can hinder polymerization and hence can adversely affect the mechanical properties of the formed cement.

Handling of the components in the open can also produce a lot of dust when the powder is poured, and monomer vapors from the liquid can enter the breathing air, which can pose a health risk—in particular allergic reactions—for the surgical team performing the mixing.

Many of these aforedescribed problems also apply to the preparation of other types of implant materials. All these disappointing experiences have over the past years prompted the development of new mixing methods, with the goal of eliminating the deficiencies mentioned above. Mixing vessels have been developed, wherein the container is firmly closed after the components have been filled in, thereby preventing the release of monomer vapors during the mixing process. Other systems perform the mixing process after the mixing vessel has been filled under reduced atmospheric pressure. In this case, the monomer vapors are typically suctioned off with a "vacuum pump" and trapped in a carbon filter.

Recently, mixing systems have been disclosed, in which polymer powder and monomer liquid are provided by the manufacturer in separate sections of the mixing system. The two components are hereby held in separate containers which can be connected. The mixing process is expected to proceed unaffected by the environment or external interference. Examples for such systems are described in the applications U.S. Pat. Nos. 4,277,184, 5,328,262, 5,549,380, 5,551,778, DE 40 30 832 and EP 0 692 229.

These systems still have significant deficiencies and disadvantages in their practical manufacture and application. The sterile manufacture of such packages poses a particularly significant problem. Essentially, only three methods can be used for sterilizing bone cements: Sterile filtration and sterile filling for the monomer; γ-ray sterilization or ethylene gassing for the polymer.

Since in conventional systems the container for the polymer powder must be the hermetically sealed to maintain sterile conditions, the powder containers are typically sterilized by γ-ray irradiation. Recent investigations have shown (Harper et al., J. of Mat. Sci.: Mat. in Med. 8, 849–853, 1997) that treatment of the cement powder with energetic radiation causes a significant deterioration in the mechanical stability of the cement and consequently a higher risk that the prosthesis mechanically loosens prematurely. It is known that a mixing system in which the containers for polymer and monomer are connected with each other, cannot be exposed to γ-irradiation since can polymerize prematurely.

In general, a system would be useful which reliably eliminates the aforedescribed disadvantages of conventional devices. Such system would be particularly useful for the modern implant materials, especially ceramic implant materials (in addition to bone cements), which have become increasingly more important. Nonporous fabrication is here of great importance, because this would make the implant materials much safer and easier to handle in the operating room.

According, there is a need for finding a solution that can be universally applied to the different implant materials in use today and that provides the advantages of ready-for-use, hermnetically sealed, pre-filled, sterile components, while simultaneously eliminating the clinical safety risks associated with conventional systems. More particularly, a mixing system would be advantageous which is not affected by external conditions and which can be operated independently of the hospital conditions, in particular in view of the availability of a compressed air supply with a suitable supply rate (quantity per minute) and supply pressure, or an electrical power source. In addition, the "vacuum source" should advantageously be integrated directly in the mixing system so that the mixing process is simple and safe. In particular, bothersome hose connections that can interfere with the operation of the system should be eliminated, since in practice such hose connections can contribute to malfunctions. Moreover, conventional pump systems are difficult to handle and to operate and are expensive to sterilize and to maintain. The novel mixing system should also be configured so that the residual pressure in the mixing vessel itself can be continuously controlled during the entire mixing process.

In the context of the minimally-invasive surgical procedures which for many reasons are advantageous and preferred in treating bone defects, the implant materials are—as described above—preferably applied locally, directly to the site of the defect.

It has been observed that in particular for the treatment of bone defects, such as fractures, pseudo-arthrosis and cysts, the injection of liquid implant materials and/or active ingredients is unsuitable and undesirable. Instead, the implants should be applied with a consistence that keeps the implants stationary at the site, i.e., at the target location, for an extended time so that they can initiate the biological reconstruction processes. In addition, implant materials should be considered which solidify in situ, which have to provide certain supporting and stabilizing functions, and which can also function as carriers for active ingredients.

This object can advantageously be achieved by applying the implant materials either in form of a paste or by applying active ingredients as part of a viscous matrix. Preferably, the matrix should solidify in situ within a specified time that is not excessive, so that the implant, optionally consisting of carrier materials and active ingredients, is available for a longer period of time at the site of the defect. It is desirable, however, that the applied matrix can be broken down and/or absorbed, so that after a certain time newly formed bone can permeate the stabilized defects which are initially filled by the matrix, thereby completely restoring the original physiological and biological characteristic of the affected skeletal part and ensuring full load bearing capability.

Such paste-like or viscous implants that can solidify in situ are frequently composed of two or more components, which are initially stored separately and subsequently combined and mixed before application. Such systems typically consist of a dry, powder component and a second liquid component. The powder(s) can include individual components or combinations of, for example, hydroxyl apatite, tri-calcium phosphate, calcium sulfate, calcium carbonate, polymers, in particular polymers based on poly-acrylates and/or poly-methacrylates, also lactide, glycolide and/or lactide/glycolide, collagen, poly-saccharide such as agarose, gelatin, fibrin and the like. The corresponding liquids include in particular liquids with an aqueous base (such as water (aqua pro injections), buffer solutions, Ringer solution, physiological saline solution, blood, serum, etc.) or suitable organic liquids, for example monomer liquids. The individual components must, of course, be combined before application and mixed to form a homogeneous, nonporous matrix. This process can be carried out using conventional mixing methods, for example mixing methods commonly used for bone cements or for the mixing and preparation of ceramic materials.

Advantageous, handling such systems, including the sterile simple and safe local application of the implant materials directly after mixing, is facilitated by providing the sterile powder component in a hermetically sealed container which can optionally be configured as a mixing system, while also providing the sterile liquid in a separate container which is also hermetically sealed. Both containers have to be supplied in a sterile double-wrapped package which is required for materials used in an operating room. After removing the containers from the package, the components in the two containers have to be combined, mixed and applied under sterile conditions.

Starting from the above discussion and the described clinical-therapeutic problems and requirements, it is the object of the present invention to find a simple and safe solution for combining implant components, as well as to solve the problem of configuring the "vacuum", mixing and storage units so that the combined system can also be used for homogeneously mixing the content, optionally under reduced atmospheric pressure, and for subsequently applying the mixture to the bone defect. In particular, the liquid injector (see below) should be hermetically sealed, in particular if it contains organic solvents, such as a monomer, for example methyl acryate/methyl methacryate, to ensure that the monomers remain stable over an extended period of time without loss of material, which cannot be achieved when using a piston. The liquid injector should also be capable of holding viscous materials or suspensions.

Starting from a device of the aforedescribed type, the object is solved by the invention in that the mixing shaft, which is guided out of the first container, is hollow and joined on its outer end with a hand-operated pump that produces the reduced pressure and connected with the hand-operated pump, that the hollow mixing shaft is provided with a through opening in an area that is sealingly guided through the container wall when the mixing shaft is completely pushed in. The through opening is connected to an admission channel which opens out in the container wall in this area and which is provided with a self-closing valve and guided into the inside of the container. A measuring device which indicates the reduced pressure in the container can be connected to the first container, and the housing of the hand-operated pump is configured for use as a handle for moving the mixing shaft.

With this configuration, the sterile content held in the separate hermetically sealed containers can be combined under sterile conditions, without bringing the content of the containers in contact with the ambient air. This is achieved in particular by the connection module, i.e., the perforation cylinder, which simultaneously perforates the foils or membranes that hermetically seal the containers when the powder container and the liquid injector are combined, and which can be easily removed at the end of the mixing process. The connection module can then be replaced with an injection nozzle for easily and safely applying the readied implant material locally.

Surprisingly, it has been found that the device of the invention can be handled much more easily and safely than conventional mixing devices. It is also been found that the invention, which uses simple building blocks, can be used to combine mixing containers filled with different types of implant materials to suit the specific, actual, practical clinical requirements. This possibility is quite advantageous and offers the clinical staff completely new therapeutic options.

Advantageous embodiments of the device of the invention are recited in the dependent claims.

BRIEF DESCRIPTION OF THE DRAWINGS

The invention will be described hereinafter in more detail with reference to an exemplary embodiment illustrated in the drawing, which shows.

DETAILED DESCRIPTION OF THE PREFERRED EMBODIMENTS

Figure 1:
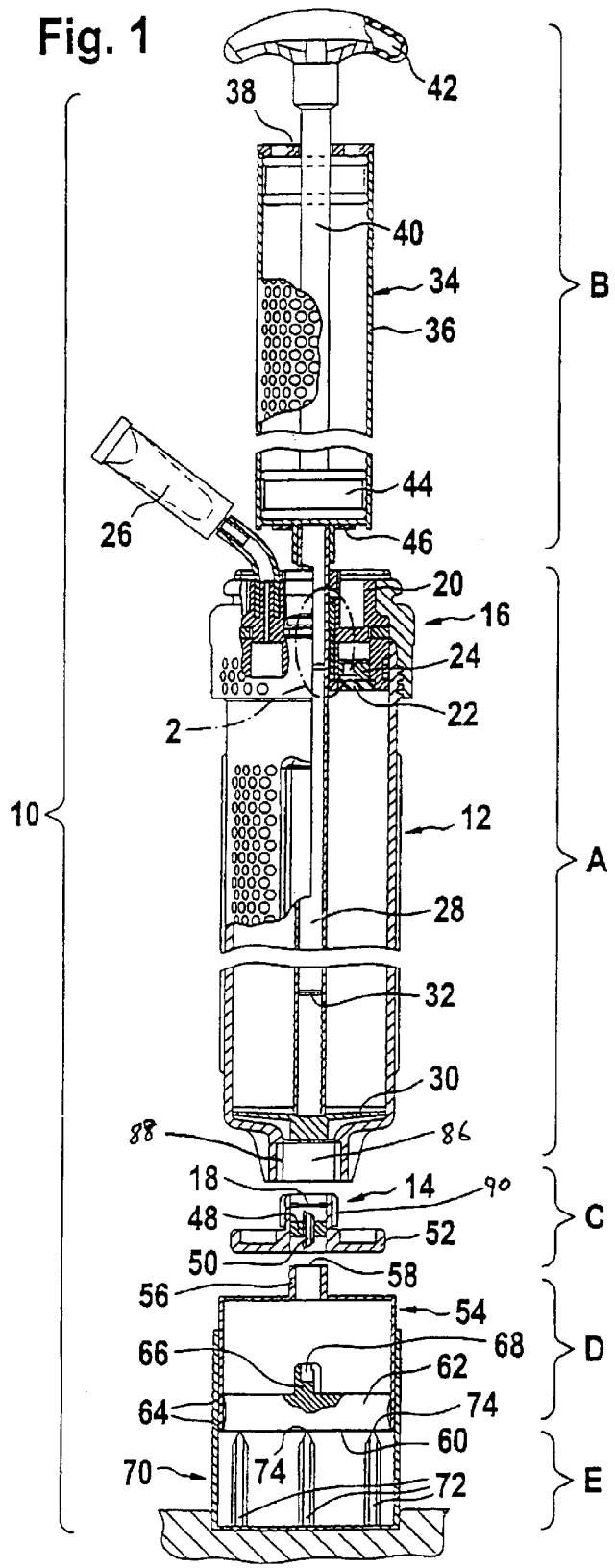
FIG. 1 a partial cross-sectional view along the longitudinal center plane and in addition, a partially cut-open view of the preparation and application device according to the invention.

The complete preparation and application device 10 of the invention combines different modular units and consists essentially of a container, the powder container A, adapted to receive an arbitrary implant material in the form of a powder or granulate, optionally in combination with one or several pharmaceutical active ingredients, an integrated vacuum pump B, a perforation cylinder C, a liquid injector D, which contains the mixing liquids, and a guide cup E.

Regarding A:

The container 12 for receiving the dry material ("powder container") is supplied to the user filled with implant material (dry components, preferably in form of a fine powder and/or granulate) and with a screwed-in perforation cylinder 14. The container 12 is secured to the perforation cylinder 14 by a seat 86 which is provided on the container 12, wherein the seat 86 for the perforation cylinder 14 is provided with an interior thread 88 and the perforation cylinder 14 is provided with a complementary exterior thread 90.

One end of the powder container is closed with a sealing cap 16. The opposite opening is closed by a lamella or disk 18 which is fixedly integrated with the perforation cylinder 14. A piston 20 which is moveable in the powder container 12 in an axial direction is inserted in the sealing cap, and also a filter disk 20, a valve 24 and a manometer 26 for measuring the reduced pressure in the powder container during the mixing process 10

The sealing cap 16 has an axial center opening, through which a mixing shaft 28 with a mixing paddle 30 and a predetermined breaking point 32 is sealingly guided.

Regarding B:

The hand-operated vacuum pump 34 is placed on the mixing shaft 28 in axial extension of the shaft. The pump consists of the pump housing 36 and a housing end wall 38. A pump shaft 40 with the handle 42 and a pump piston 44 is a guided through an axial center opening in the housing end wall 38. A valve 46 is located in the bottom of the pump housing facing the container.

Regarding C:

The perforation cylinder 14 supports in its cylindrical center opening a cylindrical disk-shaped body 48 that is displaceable in the axial direction, as well as a disk-shaped handle 52. A perforation needle 50 that is pointed on both ends is integrated in the center of the body 48.

Regarding D:

The liquid injector 54 that is adapted to receive the liquid implant components is supplied to the user with a mixing liquid already filled in. The injector 54 is tapered on one end to form a cylindrical nozzle 56 that is sealed by a foil or membrane 58. The opposing opening is also sealed by a foil or membrane 60. The liquid injector includes a piston 62 that is moveable in an axial direction and has sealing lips 64 and a central nozzle 66 with a cylindrical opening 68.

Regarding E:

The cylindrical guide cup 70 receives and guides the liquid injector. Three pushed rods 72 with a cross-shaped cross section and pointed free ends 74 are inserted in the bottom of the guide cup.

The device is operated by initially pushing the mixing shaft with the mixing device in form of a mixing paddle 30 completely into the powder container 12. The liquid injector 54 is pressed with its nozzle 56 into the cylindrical opening of the perforation cylinder 14 that is screwed into the container 12. During this operation, the membrane 58 of the nozzle 56 is perforated by one end of the perforation needle 50. Simultaneously, the nozzle 56 of the liquid injector 54 pushes the disk-shaped piston 48 of the perforation cylinder 14 towards the powder container 12, whereby the other end of the perforation needle 50 perforates the disk 18 in the perforation cylinder. This provides a continuous pathway between the powder container 12 and the liquid injector 54. The liquid injector is now pushed into the guide cup in an axial direction and hence also pressed against the tips 74 of the push rods 72. The tips perforate the foil 60 of the liquid injector 54 and push the piston 62 towards the powder container 12, whereby the liquid is injected from the liquid injector 54 through the perforation needle 50 of the perforation cylinder 14 into the mixing space of the powder container 12.

The pump shaft 40 of the hand-operated vacuum pump 34 is then moved up and down with the handle 42. The air is removed from the powder container by the action of the pump piston 44 via the two valves 24, 46 which open and close depending on the excursion of the pump piston. The reduced pressure generated in the powder container can be measured and controlled with the manometer 26 during the entire mixing process.

After the system has reached the desired reduced pressure, the pump housing 36—with the pump shaft 40 completely pushed in—is now used as a handle for operating the mixing shaft 28 with the mixing paddle 30. By moving the mixing paddle 30 up and down with a rotating motion, the dry and liquid components of the implant material are homogeneously mixed in the powder container 12 for a predetermined time. Air inclusions are removed from the implant material as a result of the reduced pressure in the system.

After completion of the mixing operation, the mixing shaft 28 is pulled out completely until the mixing paddle contacts the sealing cap 16. The portion of the mixing shaft that projects above the sealing cap is then broken of at the predetermined breaking point 32.

The liquid injector 54 together with the perforation cylinder is then unscrewed from the powder container 12 by using the handle 52. The removed components can be replaced by a nozzle ("snorkel") that is screwed into the opening of the powder container. The container can then be placed in a conventional application gun. The implantation material can be pressed out of the powder container by depressing the piston 20 with the application gun and directly applied with the nozzle into the bone support for the implant.

Figure 2:
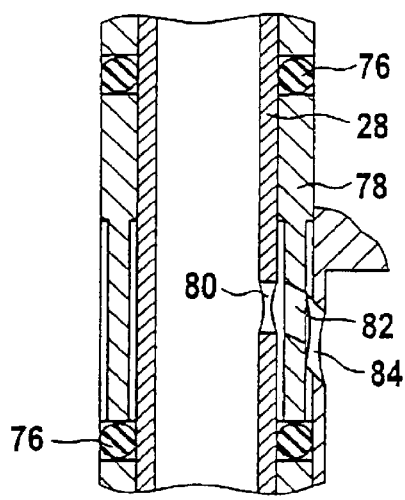
FIG. 2 a longitudinal center section of a detail located in FIG. 1 inside the dash-dotted oval 2 to illustrate the sealed guiding of the mixing shaft in the container sealing cap.

FIG. 2 shows how the mixing shaft 28 is sealed in the sealing cap 16 and in the piston 20 disposed in the sealing cap. It can be seen that the seal is provided by two longitudinally spaced-apart O-rings 76 which are arranged between a sleeve 78 that surrounds the mixing shaft 28. A through opening 80 in the mixing shaft 28 faces the sleeve 78 in the position depicted in FIG. 1 where the mixing paddle 30 is completely pushed into the container. The sleeve 78 also has a through opening 82 which terminates in a flow through channel 84 that opens into the interior of the container and is provided with the self-closing valve 24. As can also be seen, when the hand-operated pump 34 is operated by pulling out the piston 44, the vacuum produced under the piston affects in the entire interior of the container via the hollow interior of the mixing shaft 28, the through openings 80 and 82 and the flow through channel 84. The cooperation between the valves 24 in the piston and 46 in the pump 34 ensures that any generated overpressure closes the valve 24 and is exhausted to the atmosphere via the valve 46 during a downward stroke of the piston 44 in the housing 36 of the pump 34. The reduced pressure produced in the container 12 can then be lowered further by operating the hand-operated pump 34 again.

What is claimed is:

1. Preparation and application device for implant materials that include at least one powder or granular component and a liquid component and are to be prepared immediately before use, with a first container that receives the powder or granular component in a sterile, closed-off manner, and a second container which receives the liquid component in a sterile, closed-off manner, the second container connectable to the first container, wherein means are provided for producing an overflow connection between the two containers, for displacing the liquid component from the second into the first container, and for thoroughly and homogeneously mixing the components in the first container by moving a mixing device that is arranged in the first container on a hollow mixing shaft that is sealingly guided out of the container, wherein the hollow mixing shaft is joined on its outside end to a hand-operated pump for producing the reduced pressure and connected with the hand-operated pump, the hollow mixing shaft in the completely pushed-in position is provided with a through opening in its region that is sealingly guided through the container wall, with the through opening connected with a flow through channel which opens in this region into the container wall and has a self-closing valve, and the housing of the hand-operated pump is formed so that it can operate as a handle for moving the mixing shaft.

2. The device of claim 1, wherein for connecting the first container with a second container a perforation cylinder is provided, which is sealingly closed by a disk in an end region facing the first container and which can be inserted and secured in a seat provided in the first container, with a nozzle that projects from the second container and is sealed by a membrane insertable into the perforation cylinder, that in the interior of the perforation cylinder a disk-shaped body is arranged for displacement in the longitudinal direction of the perforation cylinder, through which body a hollow perforation needle extends that protrudes from both sides of the body and is pointed on both ends, and that the length of the nozzle projecting from the second container is dimensioned so that the nozzle when inserted into the perforation cylinder, which is secured in the seat of the first container, displaces the disk-shaped body towards the first container, wherein both the disk that closes the perforation cylinder as well as the membrane that seals the nozzle of the second container are pierced by the perforation needle.

3. The device of claim 2, wherein the second container is sealingly closed on its end facing the nozzle by a membrane, after which membrane there is arranged in the interior of the container a moveable piston which seals against the interior wall of the container, and that the second container is supported for displacement in a guide cup, with push rods having pointed free ends projecting from the closed bottom of the guide cup, which push rods, when the guide cup is displaced in the direction towards the nozzle of the second container, penetrate the membrane that seals the bottom of second container and displace the following piston towards the nozzle.

4. The device according to claim 2, wherein the seat for the perforation cylinder is provided with an interior thread and the perforation cylinder is provided with a complementary exterior thread.

5. The device of claim 4, wherein the perforation cylinder is provided with a handle that has a diameter greater than that of the perforation cylinder.

6. The device according to claim 1, wherein the mixing shaft, which is sealingly and displaceably guided through a sealing cap that closes the first container, is provided with a predetermined breaking point, which is located outside the container in the region of the sealing cap when the mixing shaft is completely pulled out of the first container.

7. The device of claim 6, wherein the sealing cap is penetrated by a displaceable piston which sealingly contacts the interior wall of the first container, with the end face of the piston that faces away from the interior of the container being approximately flush against the sealing cap in the initial position, but being displaceable towards a seat for a perforation cylinder by applying a force in the direction of the interior of the container.

8. The device according to claim 1, wherein the hand-operated pump disposed on the outer end of the mixing shaft for generating the reduced pressure in the first container is implemented as a piston pump having a piston arranged in the housing, with the piston being displaceable in the housing by a pump shaft that is guided out of the housing end face facing away from the first container and has a handle on its free end.

9. The device of claim 8, wherein a valve, which is self-closing when a reduced pressure is generated on the container-side in the hand-operated rump by displacing the pump piston, and which opens in the presence of an overpressure, is provided in the end face of the pump housing that is connected with the mixing shaft.

\* \* \* \* \*